(12) United States Patent  (10) Patent No.: US 8,505,554 B2
Smith  (45) Date of Patent: *Aug. 13, 2013

(54) APPLICATOR FOR A HAIR TREATMENT COMPOSITION FOR IMPROVED HAIR STRAND EFFECTS

(75) Inventor: Paul James Smith, Twickenham (GB)

(73) Assignee: The Procter & Gamble Company, Cincinnati, OH (US)

( * ) Notice: Subject to any disclaimer, the term of this patent is extended or adjusted under 35 U.S.C. 154(b) by 193 days.

This patent is subject to a terminal disclaimer.

(21) Appl. No.: 12/622,716

(22) Filed: Nov. 20, 2009

(65) Prior Publication Data

US 2010/0139683 A1    Jun. 10, 2010

(30) Foreign Application Priority Data

Dec. 10, 2008 (EP) .................................. 08021436

(51) Int. Cl.
*A45D 19/18* (2006.01)
*A61K 8/18* (2006.01)
*A61Q 5/08* (2006.01)
*A61Q 5/10* (2006.01)
*A46B 15/00* (2006.01)
*A46B 11/00* (2006.01)
*B65D 43/14* (2006.01)
*B65D 51/04* (2006.01)

(52) U.S. Cl.
USPC .............. 132/270; 132/208; 401/10; 220/848

(58) Field of Classification Search
USPC .................. 132/270, 200, 202, 207, 208, 212, 132/272, 273, 274, 234, 244, 221, 222, 108–112; 401/9, 10, 207, 196, 203, 261; 220/848; 8/405, 406, 408, 435, 151; 68/200, 205 R
See application file for complete search history.

(56) References Cited

U.S. PATENT DOCUMENTS

| 2,272,409 | A | | 2/1942 | Johnson |
| 2,310,295 | A | | 2/1943 | Keele |
| 2,761,459 | A | * | 9/1956 | Kaul ............................. 132/109 |
| 2,776,667 | A | | 1/1957 | Fitzgerald |
| 3,030,968 | A | | 2/1960 | Oberstar |
| 2,962,031 | A | | 11/1960 | Bumgarner |
| 3,128,778 | A | * | 4/1964 | Ricci et al. .................... 132/212 |

(Continued)

FOREIGN PATENT DOCUMENTS

| DE | 662702 C1 | 7/1938 |
| DE | 197639177 U1 | 4/1977 |

(Continued)

*Primary Examiner* — Vanitha Elgart
(74) *Attorney, Agent, or Firm* — Carl J. Roof; James T. Fondriest

(57) ABSTRACT

The present invention relates to an applicator which allows for precise, non-messy and even application of a hair treatment composition to a hair strand. The applicator comprises a plate movably joined by a connection to a well, a hair orientation element on the internal surface of the plate which extends towards the well and a liquid impervious, resilient fluid metering element comprising a lower metering element on the rim of the well and an upper metering element on the internal surface of the plate, wherein each independently comprise an inner and an outer surface, wherein the outer surface of the upper metering element and lower metering element independently have a convex shape. When the applicator is in a closed state, the lower metering element and the upper metering element are substantially juxtaposed to provide the fluid metering element.

18 Claims, 3 Drawing Sheets

U.S. PATENT DOCUMENTS

| | | | |
|---|---|---|---|
| 3,662,767 A | 5/1972 | Murtha | |
| 3,702,508 A | 11/1972 | Netter | |
| 3,921,647 A | 11/1975 | Fisher | |
| 4,020,854 A | 5/1977 | Caruso | |
| 4,108,184 A | 8/1978 | Morganroth | |
| 4,398,549 A | 8/1983 | Thomas | |
| 4,503,870 A | 3/1985 | Peterson | |
| 4,671,302 A * | 6/1987 | Hill | 132/212 |
| 4,796,812 A | 1/1989 | Grollier | |
| 4,942,893 A | 7/1990 | Trottier | |
| 5,042,514 A | 8/1991 | Bastien | |
| 5,060,679 A | 10/1991 | Christopher et al. | |
| 5,228,465 A * | 7/1993 | Hill | 132/212 |
| 5,279,313 A | 1/1994 | Clausen | |
| 5,535,764 A | 7/1996 | Abramson | |
| 5,554,197 A | 9/1996 | Assini | |
| 5,706,839 A * | 1/1998 | Patti | 132/277 |
| 5,771,906 A | 6/1998 | De Benedictis | |
| 5,823,204 A | 10/1998 | Todd | |
| 5,848,730 A | 12/1998 | Kawase | |
| 5,971,645 A | 10/1999 | Fukushima | |
| 6,062,231 A | 5/2000 | De Laforcade | |
| 6,148,829 A | 11/2000 | De Benedictis | |
| 6,250,312 B1 | 6/2001 | Dasilva | |
| 6,427,701 B1 | 8/2002 | Roth | |
| 6,440,175 B1 | 8/2002 | Stanley | |
| 6,626,599 B2 | 9/2003 | De LaForcade | |
| 6,746,165 B2 * | 6/2004 | de Laforcade | 401/10 |
| 6,748,957 B1 | 6/2004 | Giordano | |
| 7,025,069 B2 | 4/2006 | Thiebaut | |
| 7,156,885 B2 * | 1/2007 | Kennedy et al. | 8/405 |
| 7,198,049 B2 | 4/2007 | Elmer | |
| 7,357,137 B2 | 4/2008 | Husband | |
| 7,425,220 B2 | 9/2008 | Barrass | |
| 7,475,688 B2 | 1/2009 | Colacioppo | |
| 7,543,591 B1 | 6/2009 | Munsil | |
| 7,640,939 B2 | 1/2010 | Ploix | |
| 2002/0114657 A1 | 8/2002 | Gueret | |
| 2002/0142027 A1 | 10/2002 | Gueret | |
| 2002/0197228 A1 | 12/2002 | LaSala | |
| 2003/0007825 A1 | 1/2003 | De Laforcade | |
| 2004/0016064 A1 | 1/2004 | Vena | |
| 2004/0031502 A1 | 2/2004 | Winckels | |
| 2004/0089316 A1 | 5/2004 | Hamilton | |
| 2004/0182408 A1 | 9/2004 | De LaForcade | |
| 2005/0079192 A1 | 4/2005 | Simon | |
| 2005/0207153 A1 | 9/2005 | Leleve | |
| 2005/0211599 A1 | 9/2005 | De LaMettrie | |
| 2006/0042643 A1 | 3/2006 | Delan | |
| 2006/0064824 A1 | 3/2006 | Godfrey | |
| 2006/0090771 A1 | 5/2006 | Ramet | |
| 2006/0144415 A1 | 7/2006 | Magee | |
| 2006/0207036 A1 | 9/2006 | Kennedy | |
| 2007/0144550 A1 | 6/2007 | Roher | |
| 2007/0215170 A1 | 9/2007 | Kennedy | |
| 2007/0227620 A1 | 10/2007 | Kunii | |
| 2008/0000492 A1 | 1/2008 | Mills | |
| 2008/0083418 A1 | 4/2008 | Glenn | |
| 2008/0083419 A1 | 4/2008 | Glenn | |
| 2008/0083420 A1 | 4/2008 | Glenn | |
| 2008/0087292 A1 | 4/2008 | Abergel | |
| 2008/0087293 A1 | 4/2008 | Glenn | |
| 2008/0087294 A1 | 4/2008 | Glenn | |
| 2008/0110929 A1 | 5/2008 | Stanley | |
| 2008/0156817 A1 | 7/2008 | Roseblade | |
| 2008/0196734 A1 | 8/2008 | Husband | |
| 2008/0223386 A1 | 9/2008 | Albisetti | |
| 2008/0223391 A1 | 9/2008 | Baker | |
| 2008/0223393 A1 | 9/2008 | Boyle | |
| 2008/0257370 A1 * | 10/2008 | Perry | 132/200 |
| 2008/0308119 A1 | 12/2008 | Smith | |
| 2009/0050171 A1 | 2/2009 | Barrass | |
| 2009/0071496 A1 | 3/2009 | Glenn | |
| 2009/0084393 A1 | 4/2009 | Baker | |
| 2009/0084394 A1 | 4/2009 | Baker | |
| 2009/0084395 A1 | 4/2009 | Glenn | |
| 2009/0095314 A1 | 4/2009 | Lund | |
| 2009/0101159 A1 | 4/2009 | Bonnafous | |
| 2009/0152281 A1 | 6/2009 | Bowes | |
| 2009/0223531 A1 | 9/2009 | Lund | |
| 2010/0139684 A1 * | 6/2010 | Smith et al. | 132/208 |
| 2010/0139685 A1 * | 6/2010 | Smith | 132/208 |
| 2010/0175704 A1 * | 7/2010 | Gueret | 132/200 |

FOREIGN PATENT DOCUMENTS

| | | |
|---|---|---|
| DE | 198805283 U1 | 7/1988 |
| DE | 3138389 C2 | 7/1990 |
| DE | 4041742 A1 | 6/1992 |
| DE | 29616331 UI | 12/1996 |
| DE | 29917054 U1 | 8/2000 |
| DE | 10259016 A1 | 6/2004 |
| DE | 202004017014 U1 | 6/2005 |
| DE | 20221665 U1 | 11/2006 |
| DE | 102005058188 A1 | 6/2007 |
| DE | 202007016018 U1 | 4/2008 |
| EP | 1138374 A1 | 10/2001 |
| EP | 1566114 A1 | 8/2005 |
| EP | 1264559 B1 | 11/2005 |
| EP | 1897459 A1 | 3/2008 |
| EP | 1915920 A1 | 4/2008 |
| EP | 1481605 B1 | 8/2009 |
| FR | 2444421 A1 | 7/1980 |
| FR | 2495905 A1 | 6/1982 |
| FR | 2854778 A1 | 11/2004 |
| FR | 2905833 A1 | 3/2008 |
| GB | 274875 A | 10/1927 |
| GB | 2242357 A | 10/1991 |
| GB | 2383944 A | 7/2003 |
| GB | 2384425 A | 7/2003 |
| JP | 4-41305 | 4/1992 |
| JP | 10290712 A | 11/1998 |
| JP | 11-178630 | 7/1999 |
| JP | 11-178639 A | 7/1999 |
| JP | 2001-211925 A | 8/2001 |
| JP | 2001523500 A | 11/2001 |
| JP | 2002-034636 A | 2/2002 |
| JP | 2003-199623 A | 7/2003 |
| JP | 2003-310337 A | 11/2003 |
| JP | 2004338725 A | 12/2004 |
| JP | 2006043434 A | 2/2006 |
| JP | 2006082852 A | 3/2006 |
| JP | 3129205 U | 2/2007 |
| WO | WO 93/02589 A1 | 2/1993 |
| WO | WO 93/10687 A1 | 6/1993 |
| WO | WO 98/43511 A1 | 10/1998 |
| WO | WO 02/074129 A1 | 9/2002 |
| WO | WO 2006/010354 A1 | 2/2006 |

* cited by examiner

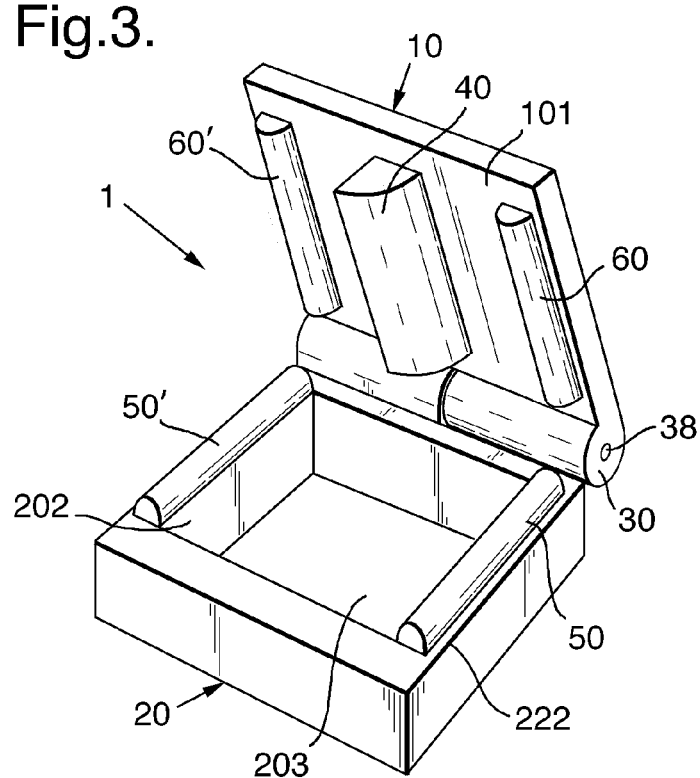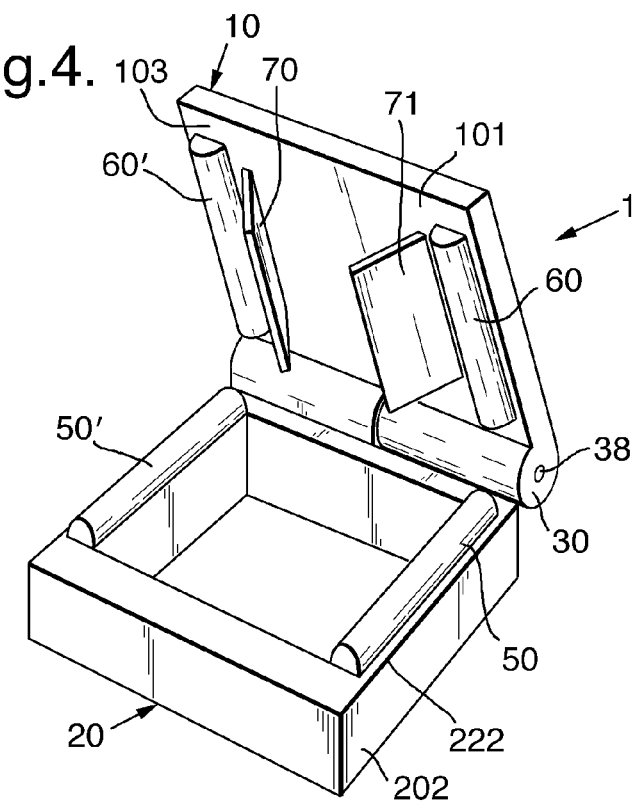

APPLICATOR FOR A HAIR TREATMENT COMPOSITION FOR IMPROVED HAIR STRAND EFFECTS

FIELD OF THE INVENTION

The present invention relates to an applicator which allows for precise, non-messy and even application of a cosmetic composition to fibres, preferably keratinous fibres. The applicator, which comprises a hair orientation means and a fluid metering means, is especially intended for a hair treatment composition to provide hair strand effects.

BACKGROUND OF THE INVENTION

Application of hair treatment compositions to distinct hair strands allows the user to achieve a different look than a full head application. Hair treatment compositions for providing a hair strand effects include highlighting compositions, dyeing compositions, perming compositions, styling compositions and mixtures thereof.

Hair strand effects such as those provided by highlighting compositions and dyeing compositions must be precisely applied where desired. For example, if a too abundant amount of highlighting composition is applied to the root, it may transfer to the neighbouring unselected hair strands. This may alter the overall end result and may totally disrupt the pattern that the user has tried to create. If an excessive amount of product is applied to the root, the colour effect will not be consistent along the length of the hair, leading to an undesired visual effect. If, instead, insufficient composition is applied to the hair strands, the evenness of the hair strand effect may not be achieved producing an end result which is visually unacceptable. Hence it is important that a consistent amount of product is applied uniformly along the hair strands being treated.

One known method for providing hair strand effects such as highlighting is the cap and hook system. A cap, provided with holes, is positioned over the head and hair strands are pulled out with a hook. Far from being accurate, the cap and hook system suffers from several drawbacks including random selection of the hair strands via the holes on the cap and the likelihood of applying the highlighting composition to only a portion of the selected hair strands and not to the root portion.

Several applicators have been designed for application of a hair treatment composition to independent bundles of hair strands as alternatives to the cap and hook system. These applicators belong to two general fields. One field comprises applicators based on combs and/or brushes. The other group comprises applicators having two articulated portions which are movable one relative to the other. Many attempts have been disclosed in this later field. U.S. Pat. No. 3,030,968 refers to an applicator for liquid treating material to be loaded by immersion. This applicator comprises a trough and a hair guide member mounted on the ends of the legs of a U-shaped resilient spring. The spring allows for manual compression and permits the hair guide member to fit into the trough. U.S. Pat. No. 6,062,231 discloses a device for applying a hair product to hair strands. This device comprises two articulated portions; the application means to be loaded by immersion and the retaining member to keep the hair strands on the applicator means while the device is in use. Another attempt is shown in US2003/0024544 wherein a device is disclosed provided with a cavity for the hair product and a retention member which is elastically deformable. The retention member may comprise porous or fibrous material and the cavity is provided with at least one notch to keep the hair strands in position during the application of the hair treatment composition. However the use of such members has a number of drawbacks, in particular the deposition of the composition is not uniform across all the hair strands and or may excessively coat the hair or not coat some hair strands at all. Moreover, the composition may also be displaced from the applicator causing mess.

It is generally recognized that the self-application of a composition to achieve hair strand effects are difficult per se, in particular those for highlighting and dyeing. To achieve the expected end results, an applicator capable of facilitating the self-application of a hair treatment composition needs to be conceived to address several technical challenges, but in particular, the applicator should evenly apply the composition to independent bundles of hair strands. Evenness is very important when the composition is a highlighting or dyeing composition. The permanent effect provided by these compositions is not immediately visible after the application and if the result is not appealing, it is not easily reversed. An applicator should hence ensure homogeneous coating along the length and width of the bundle of hair strands and likewise on the front and rear surfaces.

In addition, such applicators should apply an amount of hair treatment composition, which is sufficient to coat all of the hair strands and thereby provide a hair strand effect without transferring to neighbouring strands or the scalp and skin. Furthermore, the applicator should not apply, but then subsequently scrape off the hair treatment composition while the user moves the applicator along the bundle of hair strands. The application of the composition with such an applicator should also occur in a tidy and clean fashion without the hair treatment composition leaking out of the hair treatment applicator. The applicator should also allow the movement of hair through the applicator without hindering its path resulting in snaring, entanglement and potentially discomfort to the user.

Finally, such an applicator for hair treatment compositions should be easy to use; it should be cheap and easy to manufacture and it should not require any special experience and training in matters such as how much and where to load the hair treatment composition. Ideally, the consumer should be able to load and use the applicator by simply following a few instructions provided by the manufacturer to achieve the desired result.

Thus, what still remains to be solved in the art is a hair treatment applicator capable of overcoming the technical problem defined above.

It has now been found that an applicator, as defined herein after can significantly improve the application of a hair treatment composition to provide hair strand effects.

SUMMARY OF THE INVENTION

According to the present invention, an applicator (1) for applying a hair treatment composition to the hair is provided, wherein said applicator (1) comprises a plate (10) and a well (20), wherein said plate (10) and said well (20) are movably joined by a connection (30) so that the applicator (1) may alternate between a closed and an open state, and wherein said plate (10) has an external surface (102) and an internal surface (101), and said internal surface (101) comprises at least one hair orientation means which extends beyond said internal surface (101) towards said well (20), and wherein said well (20) comprises a rim (222) and wherein said applicator (1) further comprises a liquid impervious, resilient fluid metering means, wherein said fluid metering means comprises a lower metering means (50) positioned on said rim (222) of said well (20), and an upper metering means (60) positioned on said internal surface (101) of said plate (10), wherein said lower and upper metering means (50, 60), each independently comprise an inner and an outer surface, wherein said outer surface of said upper metering means (60) and said outer surface of said lower metering means (50) independently have a convex shape and wherein when said applicator (1) is in said closed state, said lower metering means (50) and said upper metering means (60) are substantially juxtaposed to provide said fluid metering means.

Furthermore, a method to apply a hair treatment composition to a hair strand whereby said hair strand is contacted with said applicator (1) according to the invention and a kit-of-parts comprising an applicator (1) according to the invention are also described.

BRIEF DESCRIPTION OF THE DRAWINGS

FIG. 3 is a perspective view of an embodiment of said applicator (1) according to the invention. Said plate (10) is movably joined to said well (20) by a connection (30). A member (40), which has a substantially pyramidal frustum form, projects from said internal surface (101) of said plate (10). A lower metering means (50) is laid upon said rim (222) in two portions (50; 50'), and an upper metering means (60) is laid upon the internal surface (101) of said plate (10) in two portions (60; 60').

FIG. 4 is a perspective view of an embodiment of an applicator (1) according to the invention. Said applicator (1) comprises a plate (10) connected by a connection (30) to a well (20). Said connection (30) comprises two female parts fixed by a pin (38). A lower metering means (50) is laid upon said rim (222) in two portions (50; 50'). An upper metering means (60) is laid upon said internal surface (101) along said perimeter (103) in two portions (60; 60'). Two substantially identical fins, a first fin and a second fin (70; 71) project from the internal surface (101) to form the hair orientation means.

DETAILED DESCRIPTION OF THE INVENTION

For the purpose of this invention, the term hair refers to both living hair i.e. on a living body and to non-living hair i.e. in a wig, hairpiece or other aggregation of non-living keratinous fibre. Mammalian, preferably human hair is intended.

For the purpose of this invention, the term "laid upon" is generally used to indicate the location of the feature to which it refers and not the act of locating it.

The present invention is characterized by the synergistic relationship that the features as described herein have when combined together in the specific relationship selected within the present invention to solve the above technical problem.

Figure 1:
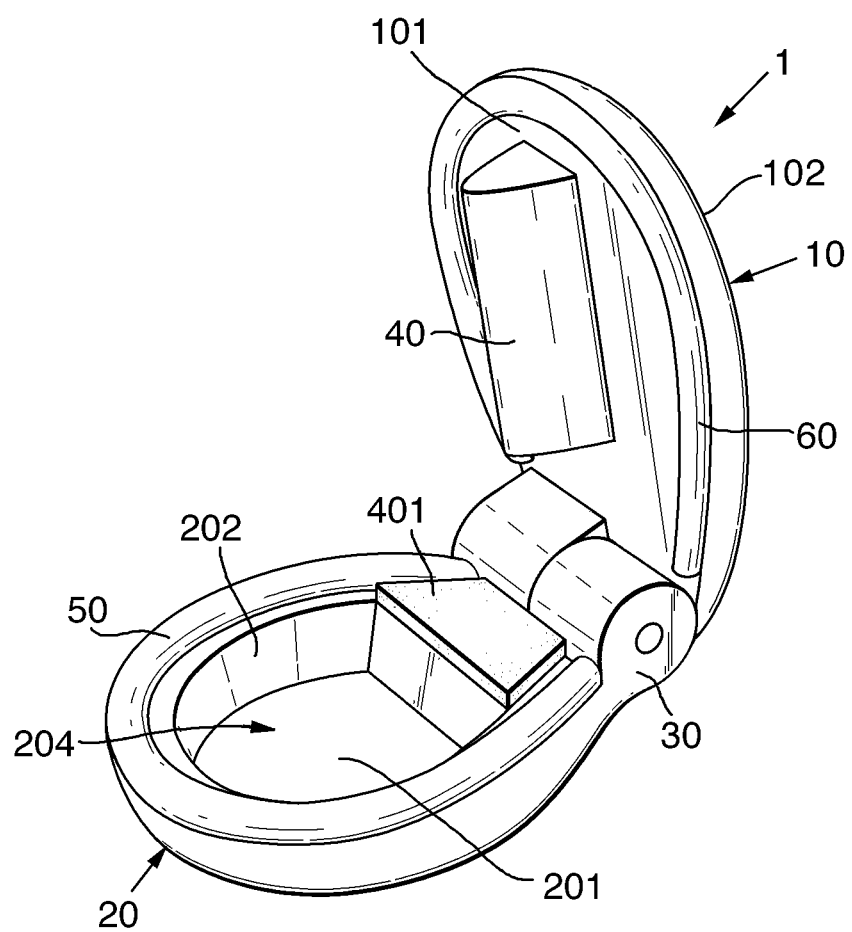
FIG. 1 is a perspective view of an embodiment of said applicator (1) according to the invention. Said applicator comprises a plate (10), a well (20) and a connection (30). In this embodiment, a lower metering means (50), is laid upon said rim (222) of said wall (202) of said well (20) and a upper metering means (60) is laid upon the internal surface (101) of said plate (10) along said perimeter (103) of said plate (10) and a hair orientation means which is a member (40) that projects from said internal surface (101) of said plate (10). The applicator (1) is shown herein in an open state, whereby said internal surface (101) of said plate (10) is in a distant relationship to the opening of said well (20). On the base (201) of said well (20) adjacent to said wall (202) at the side of the connection (30) said applicator (1) comprises a sealing means (401).

To achieve the technical effect described herein, the applicator (1) for applying a hair treatment composition to the hair according to the present invention comprises a plate (10) and a well (20) as shown in FIG. 1. A connection (30) movably joins said plate (10) to said well (20). Said plate (10) comprises a perimeter (103) and an internal (101) and an external surface (102). Said well (20) is formed by a base (201) and a wall (202), said wall (202) emerging from said base (201) and extending upwardly. Said wall (202) comprises a rim (222), said wall (202) and said rim (222) define an opening (203) and an internal volume (204) of said well (20) as shown in FIG. 1 and FIG. 3. Said plate (10) and said well (20) are movably joined by said connection (30), so that said applicator (1) can alternate from an open state to a closed state. In this latter state, said internal surface (101) of said plate (10) is in a juxtaposed relationship to said opening (203) of said well (20).

Said internal surface (101) of said plate (10) further comprises at least one hair orientation means, which in FIG. 1 is a member (40) which extends beyond said internal surface (101) towards said well (20), preferably towards but not touching said base (201) of said well (20), when said applicator is in a closed state.

Said applicator (1) further comprises a liquid impervious, resilient fluid metering means. Said fluid metering means comprises a lower metering means (50) and an upper metering means (60). Said lower metering means (50) is laid upon said rim (222) of said wall (202) of said well (20) as seen in FIGS. 1 to 4. Said upper metering means (60) is laid upon said internal surface (101) of said plate (10), preferably along said perimeter (103) of said plate (10). Said lower (50) and upper (60) metering means each independently comprise an inner and outer surface, wherein said outer surface of said upper metering means (60) and said outer surface of said lower metering means (50) independently have a convex shape. Preferably, each outer surface of said upper metering means (50) and said lower metering means (60) has a semi elliptical cross section across their entire lengths, which is preferably uniform across their entire lengths. More preferably, each outer surface of said upper metering means (50) and said lower metering means (60) has a tubular shape or partially tubular shape and is at least partially hollow and preferably entirely hollow. Said lower metering means (50) and said upper metering means (60) are positioned such that when said applicator (1) is in said closed state, said lower metering means (50) and said upper metering means (60) are substantially juxtaposed to provide said fluid metering means.

The combination of said hair orientation member (2) and fluid metering means comprising a lower metering means (50) and an upper metering means (60) as described below enable said applicator (1) to perform an application of a hair treatment composition to a hair strand, not only in a clean and non-messy fashion, but also evenly to provide an effective hair strand effect.

1. Applicator

The applicator (1) according to the present invention comprises a plate (10) movably joined to a well (20). Said plate (10) and said well (20) of said applicator (1) according to the invention are of ergonomic size and can thus fit easily on either hand. Said internal surface (101) preferably has a surface area of from about 2 cm$^2$ to about 150 cm$^2$, preferably from about 2 cm$^2$ to about 70 cm$^2$, more preferably from about 3 cm$^2$ to about 50 cm$^2$ and even more preferably from about 4 cm$^2$ to about 30 cm$^2$. The shape of said plate (10) may vary. Rectangular, square, circular, elliptical, oblong shape or combination thereof may be useful as they are easy to manufacture but other shapes, particularly those that are easily recognized by the consumers may also be used.

Said plate (10) of said applicator (1) comprises an axis Y. Axis Y extends straight from the centre of said plate (10) and transversally crosses said connection (30), preferably substantially perpendicular to said connection (30).

Said plate (10) comprises a perimeter (103), an internal surface (101) and an external surface (102). Said well (20) comprises a base (201), a wall (202) and said wall (202) comprises a rim (222). Said rim (222) defines an opening (203) and an internal volume (204) of said well (20). Said internal volume (204) is preferably for containing a hair treatment composition.

Preferably, said perimeter (103) of said plate (10) and said rim (222) of said wall (202) of said well (20) may be curvilinear or sharp. Said perimeter (103) of said plate (10) and said rim (222) of said wall (202) of said well (20) have each independently a length. Preferably, said perimeter (103) and said rim (222), have substantially identical lengths. Said rim (222) also comprises a width. Preferably, said width of said rim (222) is from about 1 mm to about 20 mm, more preferably from about 2 mm to about 15 mm, even more preferably from about 3 mm to about 8 mm.

Figure 2:
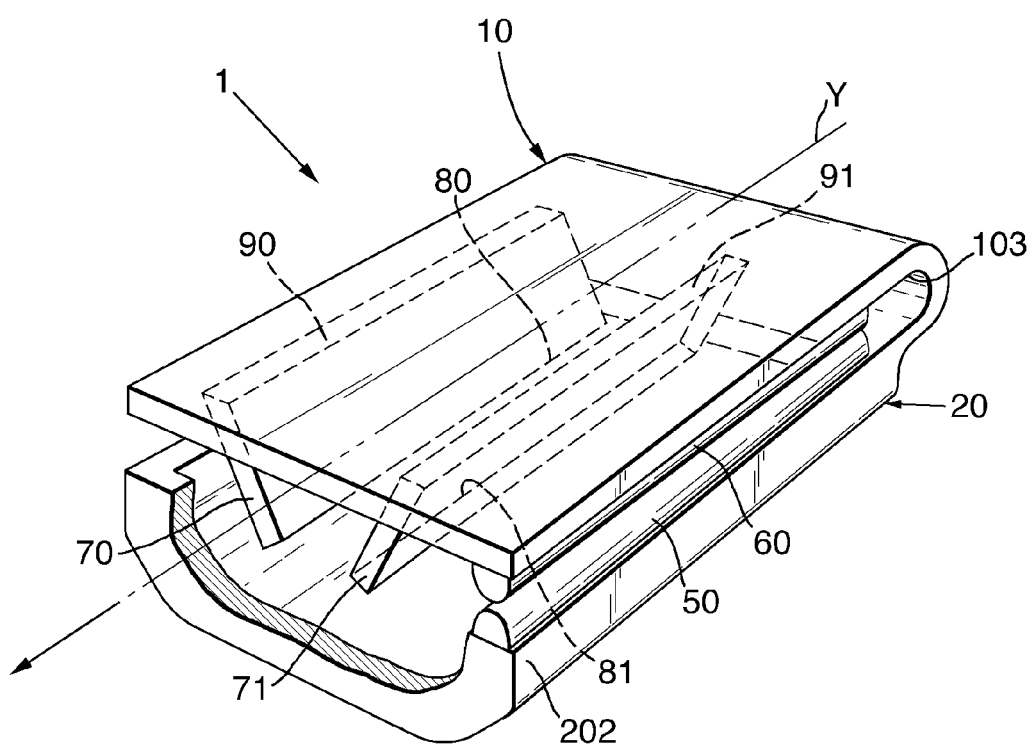
FIG. 2 is a perspective view of an embodiment of the applicator (1) according to the invention. The applicator (1) is shown in this embodiment in a closed state. Part of said wall (202) of said well (20) has been removed to show that said internal surface (101) of said plate (10), which in this embodiment is substantially flat, and a hair orientation means which comprises two substantially identical fins, a first fin (70) and second fin (71) which project in a way that said proximal edges (90; 91) are substantially parallel to said axis Y and said distal edges (80; 81) verge one toward the other. A lower metering means (50) is laid upon said rim (222) of said wall (202) and an upper metering means (60) is laid upon said substantially flat internal surface, along said perimeter (103) of said plate (10).

Said internal surface (101) of said plate (10) may be substantially flat as shown in FIG. 2 or may be concave, convex or have a waved pattern. Said external surface (102), said wall (202) and said base (201) may also be substantially flat, concave, convex or waved. Preferably, said base (201) of said well (20) is substantially flat.

Said plate (10) and said well (20) may be manufactured from any known material or combination of materials capable of supporting a hair treatment composition. Suitable materials are polymer resins such as a polyolefins e.g. polypropylene, polyethylene or polyethylene terephthalate. Other materials which could be used include polyvinylchloride, polyamide, acetyl, acrylonitrile butadiene styrene, acrylic, acrylonitrile styrene acrylate, ethylene vinyl alcohol, polycarbonate, polystyrene, silicone or thermo plastic elastomer, thermo plastic vulcanate or copolymers where appropriate; flexible pliable substrates such as paper boards, metal based substrates and aluminium foils, filmic substrates or multiple laminations or combinations of multiple layers of said materials.

The method of manufacture of said plate (10) and said well (20) may include, but is not limited to, injection moulding, co-injection moulding, over moulding, in-mold assembly, compression moulding, blow moulding, thermo or vacuum forming of a blister type shell and lamination onto a carrier plastic or board material in the horizontal or vertical plane.

A connection (30) movably joins said plate (10) and said well (20) such that it is possible for said applicator (1) to alternate from an open state to a closed state. Said applicator (1) is shown in FIG. 2 in a closed state. When said device (10) is in a closed state, said lower metering means (50), is in a substantially juxtaposed relationship to said upper metering means (60).

Said plate (10) and said well (20) are connected via any suitable means that fulfils the above described requirements for a connection (30), including the user's hand, for example through the thumb and index finger. In one embodiment, said plate (10) and said well (20) are mounted at the ends of the arms of a tweezers-like or tong-like connection (30). In another embodiment said plate (10) and said well (20) are connected via one or more hinges, preferably one hinge. Preferably, said connection (30) is contiguous and located adjacent to said perimeter (103) of said plate (10) and to said rim (222) of said well (20).

A connection (30) is necessary to improve the user's perception of control over the applicator (1) and to allow the user to guide the applicator (1), with the use of either hand, precisely and easily to each bundle of hair strands.

2. Hair Orientation Means

The applicator (1) of the present invention further comprises at least one hair orientation means. Said hair orientation means projects from said internal surface (101) of said plate (10). The presence of said hair orientation means ensures that during use the hair strand is bent within said well (20). Without wishing to be bound by theory it is believed that the hair orientation means enables said hair strand, preferably said bundle of hair strands, to contact said hair treatment composition within said internal volume (204) of said well (20) and not only at said opening (203) of said well (20). This improves the evenness of the application, in particular, the evenness from the root to the tip of the bundle of hair strands as described herein after.

In one embodiment of the present invention, said hair orientation means is a member (40), which projects from said internal surface (101) of said plate (10), wherein said member (40) preferably has a substantially pyramidal frustum form, as shown in FIG. 3. Said member (40) may have various forms including, but not limited to, a parallelepiped form, a cube form, a cylinder form, a conical or a pyramidal form. Said member (40) may also be composed of a plurality of independent units grouped together; said independent units may comprise bristles, teeth or tines.

Said member (40) projects from said internal surface (101) of said plate (10) with a maximum height (H) and extends along said internal surface (101) with a maximum width (W) and a maximum length (L). Said member (40), preferably projects orthogonally to said axis Y with said maximum height (H). Said member (40) may extend along said internal surface (101) of said plate (10) with its maximum length (L) either along said axis Y or substantially parallel to said axis Y or transversally to said axis Y.

Preferably, said maximum length (L) is at least twice said maximum width (W). The maximum length (L) is preferably from about 20.0 cm to about 0.2 cm, more preferably from about 15.0 cm to about 0.3 cm, even more preferably from about 10.0 cm to about 0.5 cm. The maximum width (W) is preferably from about 2.5 cm to about 0.01 cm, more preferably from about 1.0 cm to about 0.02 cm, even more preferably from about 0.5 cm to about 0.03 cm. The maximum height (H) is preferably from about 5.0 cm to about 0.1 cm, more preferably from about 2.5 cm to about 0.2 cm, even more preferably from about 1.5 cm to about 0.3 cm.

When said applicator (1) is in a closed state, said member (40) does not contact said base (201) of said well (20), so that a passage is left and said hair strand, preferably said bundle of hair strands, is not constrained during use.

In another embodiment according to the invention, said hair orientation means comprises a first fin (70) and a second fin (71), which independently project from said internal surface (101) of said plate (10) as shown in FIG. 2, wherein each fin (70; 71) has a free distal edge (80; 81); wherein the free distal edge (80) of the first fin (70) points towards the free distal edge (81) of the second fin (71). The term "fin" within the scope of the present invention defines a strip or sheet of material, preferably of substantially constant thickness as described below. The form of said first (70) and second (71) fin may vary; preferably said first (70) and second (71) fin have the form of a parallelepiped wherein two of the six faces extend for an area which is at least twice the area of the other four faces. These two faces have preferably a substantially flat surface. The shape of said first (70) and second (71) fin may vary. Rectangular, square, circular, elliptical, oblong or combination thereof may be useful. A rectangular shape as shown in FIG. 2 is preferred.

Said first fin (70) projects from said internal surface (101) of said plate (10) and extends for an average first length (L1) of from about 2 mm to about 30 mm. Said second fin (71) extends independently from said first fin (70) for an average second length (L2) of from about 2 mm to about 30 mm. Preferably said first (70) fin and said second (71) fins project independently from said internal surface (101) of said plate (10) and extend with substantially identical average first and second lengths (L1; L2). Each of said first (70) and second (71) fin has a distal edge (80; 81) and a proximal edge (90; 91). Said proximal edge (90; 91) are those attached to said internal surface (101) of said plate (10) as shown in FIG. 2A. Said proximal edges (90; 91) are each independently delimited by an average width (W1) for said first fin (70) and an average width (W2) for second fin (71) and each independently by average thickness (T1) for said first fin (70) and an average thickness (T2) for said second fin (71). Said average width (W1) and (W2) are preferably of from about 20 cm to about 0.5 cm, more preferably from about 15 cm to about 1.0 cm and even more preferably from about 10 cm to about 1.5 cm. Said average thicknesses (T1) and (T2) are preferably from about 5 mm to about 0.1 mm, more preferably from about 4 mm to about 0.5 mm, even more preferably from about 3 mm to about 0.5 mm. Preferably, said distal edges (80; 81) have also substantially identical average widths (W1) and (W2) and substantially identical average thicknesses (T1) and (T2) as those proximal edges (90; 91). Said first and second fins (70; 71) may have protrusions (75) or may be embossed, especially to provide visual or tactile decoration.

Preferably said first (70) and second fins (71) are substantially identical and project in a way that said proximal edges (90; 91) are substantially parallel to said axis Y and said distal edges (80; 81) verge one toward the other as shown in FIG. 2. Preferably said proximal edge (90) of said first fin (71), more preferably said proximal edge (90) of said first fin (71) and said proximal edge (91) of said second fin (71) project from said internal surface (121) substantially parallel to said axis Y of said plate (120) as shown in FIG. 2.

Said hair orientation means may be provided in a variety of materials as previously described herein to manufacture the plate (10) or well (20) and be manufactured independently of said applicator (1). Preferably said hair orientation means is fluid impervious. More preferably said hair orientation means is selected from polyolefins, thermo plastic elastomers and mixtures thereof. In certain embodiments, both the said first (70) and second (71) fin and said plate (10) may be manufactured within the same injection or co-injection mould for example from a thermo plastic elastomer.

3. Fluid Metering Means

The applicator (1) according to the present invention is characterized by a liquid impervious, resilient fluid metering means, comprising a lower metering means (50) and an upper metering means (60) as described herein. Said lower metering means (50) is positioned upon said rim (222) of said well (20). Said upper metering means (60) is positioned upon said internal surface (101), more preferably along said perimeter (103) of said plate (10). The upper (60) and lower (50) metering means each independently comprise an inner and an outer surface, wherein said outer surface of said upper metering means (60) and said outer surface of said lower metering means (50) independently have a convex shape and wherein when said applicator (1) is in said closed state, said lower metering means (50) and said upper metering means (60) are substantially juxtaposed to provide said fluid metering means.

Without wishing to be bound by theory, it is believed that by having said liquid impervious, resilient fluid metering means comprising a lower metering means (50) laid upon said rim (222) of said well (20) and an upper metering means (60) laid upon said internal surface (101) of said plate (10), preferably along said perimeter (103), wherein the upper (60) and lower (50) metering means each independently comprise an inner and an outer surface, wherein said outer surface of said upper metering means (60) and said outer surface of said lower metering means (50) independently have a convex shape and whereby said lower metering means (50) and said upper metering means (60) are substantially juxtaposed when said applicator (1) is in a closed state; allows said applicator (1) not only to apply the hair treatment composition, but to even said application along the entire hair strand.

The term resilient as used herein refers to the ability of the means to be deformed upon the application of pressure and return to its relaxed position upon release of the pressure. As used herein the term outer surface of the upper metering means (60) refers to surface of the upper metering means which is not in direct contact with the internal surface (101) of said plate (10) and the term inner surface refers to the surface in contact with the internal surface (101) of said plate. Similarly, the term outer surface of the lower metering means (50) refers to the surface of the lower metering means (50) which is not in direct contact with the rim (222) and the term inner surface refers to the surface which is in direct contact with the rim (222).

Evenness is important in the application of a hair treatment composition, especially when said hair treatment composition is a highlighting composition or a dyeing composition. The permanent effect provided by those compositions is not immediately visible after the application and if the result is not appealing, it is not easily reversed. An applicator should hence ensure homogeneous application along the length, from root to tip, of said bundle of hair strands and likewise also on the front and rear surfaces and across the width of the bundle of hair strands. Therefore, it is not only the amount of hair treatment composition which is applied that is important but also the way it is applied. The applicator (1) according to the invention is not only designed to facilitate the application of a hair treatment composition to a hair strand, preferably to a bundle of hair strands. Said applicator (1) also avoids that said hair treatment composition is neither applied in excessive amount nor removed from said hair strand while the applicator (1) is used, so to obtain a very homogeneous and reproducible application, without the hair movement being impaired by tangling or snagging during use. In particular, the convex shape of the outer surface of said upper (60) and lower (50) metering means ensures that no pressure points are generated during use that consequently scrape the composition off the hair. The resilience also ensures that in the absence of hair, in a closed position, the applicator forms a seal to prevent any composition leaking out, whilst in the presence of hair, it can deform and enable the hair and a controlled amount of composition to pass through.

Said lower metering means (50) may be laid upon said rim (222) in a continuous or discontinuous manner, preferably in a continuous manner. By discontinuous is meant that said metering means may form loci or islets or may be interrupted. In one embodiment, said lower metering means (50) is laid upon the entire rim (222) of said wall (202) so that said rim (222) is not substantially visible and is entirely covered by said first metering means (50). In another embodiment, said lower metering means (50) is laid upon only a section or a plurality of sections of said rim (222), for example only a section of said length of said rim (222) may comprise said lower metering means (50) as shown in FIG. 2. Similarly, said upper metering means (60) is laid on the internal surface (101) of said plate on substantially the entire surface thereof, a section thereof, along a section or substantially the entire perimeter edge, preferably along substantially the entire perimeter edge. In one embodiment, the upper metering means (60) may extend along substantially the entire perimeter edge or in another embodiment only a section or a plurality of sections of the perimeter edge will comprise said upper metering means (60). Preferably said lower metering means (50) and said upper metering means (60) are positioned adjacent to said connection (30). In another embodiment, said upper metering means (60) is positioned substantially parallel to the perimeter (103) of said internal surface (101) of said plate (10) and said lower metering means (60) is positioned substantially parallel to the rim (222) of said well (20). In each embodiment, however, the lower metering means (50) and the upper metering means (60) are positioned such that when said applicator is in a closed state said lower metering means (50) and said upper metering means (60) are substantially juxtaposed. The term juxtaposed as used herein includes embodiments wherein either of said lower (50) or upper metering means (60) is larger than the other means. Preferably, the lower and upper metering means (50, 60) are substantially mirror images of one another, and are preferably directly aligned. In another embodiment said lower (50) and upper (60) metering means are positioned on the respective rim (222) and internal surface (101) wherein the lower (50) and the upper (60) metering means have a substantially juxtaposed, but staggered configuration, preferably said lower (50) and upper (60) metering means are also mirror images of one another. In a particularly preferred embodiment, said lower metering means (50) and said upper metering means (60), both comprise two portions (50; 50'), (60; 60'). More preferably each of said portions (50, 51') (60, 60') are located adjacent the ends of said connection (30). It should be noted that the references 50 and 60 are used to refer to the lower and upper metering means respectively as well as the respective portions thereof. Preferably, each of said lower metering means (50) and said upper metering means (60) has a substantially semi-elliptical outer surface and more preferably each of said outer surfaces has a semi-elliptical cross section across its entire length, which is preferably uniform across the entire length. In an alternative preferred embodiment, said upper and lower metering means (50, 60) independently have a tubular shape or a partially tubular shape and are preferably partially or entirely hollow.

When said applicator (1) according to the invention comprises a member (40) as a hair orientation means said lower metering means (50) is laid upon said rim (222) and said upper metering means (60) is laid upon the internal surface (101) of said plate (10) to be in correspondence to said member (40) as explained herein below. When said applicator (1) comprises a member (40) for example as shown in FIG. 3, said member (40) extends along said internal surface (101) with a maximum length. The application of a hair treatment composition with an applicator (1) according to the invention is performed by locating said hair strand between said plate (10) and said well (20) and preferably said hair strand is located substantially transversal to said maximum length L of said member (40). To achieve an even application, said inner surface of said lower metering means (50) is preferably laid upon a portion of said rim (222) and said inner surface of said upper metering means (60) is laid upon a portion of the internal surface (101) which are substantially parallel to said maximum length L of said member (40) when said applicator is in a closed state, and whereby said lower and upper metering means (50; 60) are substantially juxtaposed.

In another embodiment of the present invention as shown in FIG. 2, said hair orientation member comprises a first and a second fin (70; 71) as said hair orientation member (2). Said proximal edges (90; 91) of said first and second fins (70; 71) are substantially parallel to said axis Y of said plate (10). In this embodiment said lower metering means (50) is preferably laid upon a portion of said rim (222) and similarly said upper metering means (60) which are substantially parallel to said proximal edges (90; 91) of said fins (70; 71) when said applicator (1) is in a closed state.

Clearly, for both the embodiments discussed above, said lower (50) and upper (60) metering means may be discontinuous and laid upon said rim (222) of said wall [(222)] (202) and said internal surface (101) of said plate (10) respectively on both sides parallel to said maximum length of said member (40) or of said distal edges (90; 91) of said first and second fins (70; 71) as shown in FIG. 4.

Preferably, when an applicator (1) according to the invention comprises a sealing means (401) as described below, on said rim (222) of said well (202), said lower metering means is laid upon said rim (222) adjacently to said sealing means (401) either touching said sealing means (401) or not.

Said lower and upper metering means (50; 60) may independently have a length of from about 3 mm to about 40 cm, preferably from about 5 mm to about 10 cm, more preferably from about 8 mm to about 5 cm. Said lower and upper metering means (50; 60) may independently have a constant or variable width along said lengths. Said lower and upper (50; 60) metering means may independently have a maximum width of from about 1 mm to about 20 mm, preferably from about 2 mm to about 15 mm, more preferably from about 3 mm to about 8 mm.

Preferably, said lower and upper metering means (50; 60) have substantially identical widths and substantially identical lengths and they are laid upon said rim (222) and said internal surface (101) along said perimeter (103), respectively, so that when said plate (10) is brought into a juxtaposed relationship to said opening (203) of said well (20), said upper metering means (60) is substantially a mirror image of said lower metering means (50). Even more preferably said lower and upper metering means (50; 60) have substantially identical and constant widths and lengths.

The fluid metering means comprising a lower (50) and upper (60) metering means are preferably independently selected from a polymer resin such as a polyolefin e.g. polypropylene, polyethylene or polyethylene terephthalate, polyvinylchloride, ethylene vinyl acetate, polyurethane, polytetrafluoroethylene, polystyrene, natural rubber, latex, nylon, nitrile, silicone; thermo plastic elastomer (TPE) or copolymers where appropriate, closed cell foams of polyurethane; polyolefins or thermoplastic elastomers may also be used or a flexible pliable substrate such metal based substrates and aluminium foil, or multiple laminations or combinations of multiple layers of said materials. Preferably, said upper and lower metering means (60, 50) are made from a thermoplastic elastomer. The fluid metering means of the present invention may also include composite materials having one or more plies of the same or different materials superimposed physically, joined together continuously (laminated), in a discontinuous pattern, or by bonding the external edges at discrete loci.

Said lower and upper metering means (50; 60) may be attached by any suitable method to said rim (222) and to said internal surface (101) of said plate (10), respectively, providing that said method does not destroy or alter the performance of said metering means (50; 60). Said lower and upper metering means (50, 60) are preferably attached on their respective inner surfaces to said rim (222) and said internals surface (101).

The present inventors have surprisingly found that to satisfactorily apply a hair treatment composition to a hair strand, said hair strand needs not only to come into contact with said hair treatment composition which has been loaded into said applicator (1), but also said hair treatment composition should be evenly applied onto said hair strand without being removed while the application occurs.

To apply a hair treatment composition with an applicator (1) to a hair strand, preferably to a bundle of hair strands, said hair strand is located substantially straight between said plate (10) and said well (20), where a hair treatment composition has been previously loaded. Said plate (10) comprises a hair orientation means to bend said hair strand into said well (20).

Without wishing to be bound by theory, it is believed that when said applicator (1) comprises a fluid metering means as described herein, a hair treatment composition is more evenly distributed from root to tip along a bundle of hair strands, and likewise also on the front and rear surfaces and across the width of the bundle of hair strands. Thus, if an excessive amount of said hair treatment composition is applied, said metering means may distribute it evenly and homogeneously along the length of said hair strand but without removing it.

4. Additional Features

The applicator (1) may further comprise one or more sealing means, preferably one sealing means (401) is present within the hair treatment applicator (1). Said sealing means (401) may be located on the base (201) of said well (20) adjacent to said wall (202) at the side of the connection (30) or on said internal surface (101) adjacent to said connection (30). Preferably said sealing means (401) is adjacent said connection (30).

The sealing means (401) is provided to avoid displacement of hair treatment composition towards the connection (30) and hair from being trapped within said connection (30) when said internal surface (101) of said plate (10) is brought into a juxtaposed relationship to said opening (203) of said well (20). Useful materials to manufacture a sealing means (401) include those described herein for said first fin (71) and foams.

One or more stop mechanisms may be incorporated onto said applicator (1). The stop mechanism collaborates with said connection (30) to ensure that when said internal surface (101) of said plate (10) is brought into a juxtaposed relationship to said opening (203) of said well (20), the average distance between said perimeter (103) and said rim (222) is controlled. In one embodiment, two stop mechanisms are comprised on said rim (222) of said wall (201) of said well (20), preferably said two stop mechanisms are two substantially identical hemispheres. Useful materials to manufacture a stop mechanism are previously described herein to manufacture the plate (10) or well (20) described herein.

The applicator (1) disclosed herein may further comprise gripping areas on the external surfaces (102) of said plate (10) and/or on said base (201) of said well (20). Said gripping areas are designed to provide grip. Gripping means may be provided as fastening means to accommodate the user's fingers.

Fingers may be used to select the hair strands on which the hair treatment composition should be applied. The applicator (1) of the present invention may however be further provided with hair strand selection means. Examples of hair strand selection means are, but not limited to, spikes, hooks, crochets, clips or beads. The hair strand selection means may be incorporated onto said plate (10) and/or said well (20). Said means may also be attached through a snap mechanism to said plate (10) and/or said well (20) such that the hair strand selection means may swing from a position proximal to said plate (10) and/or said well (20) to a far one, such as happens with the blades of a penknife. The hair strand selection means may also be separately provided to the applicator (1) of the present invention as a component of a kit as described herein below.

5. Method of Use

The present invention also relates to a method to apply a hair treatment composition with said applicator (1) according to the invention to a hair strand, preferably a bundle of hair strands, wherein said applicator (1) comprises said hair treatment composition and whereby said hair strand is contacted with said applicator (1). Said applicator (1) may be pre-loaded with one or more hair treatment compositions, but preferably one or more hair treatment compositions are loaded into said applicator (1) before the contact of said hair strand, preferably said bundle of hair strands, with said applicator (1).

The hair treatment compositions may be a single hair treatment composition or may be formed by a first hair treatment composition which requires mixing with a second hair treatment composition before application to the hair. Preferably, said first and second hair treatment compositions are mixed to form a third hair treatment composition. Said third hair treatment composition is loaded in said hair treatment applicator (1) before contacting the hair strand, preferably a bundle of hair strands, with said hair treatment applicator (1).

Once the hair treatment applicator (1) is loaded with one or more hair treatment compositions, the user holds through the external surfaces (102) of said plate (10) and base (201) of said well (20) of said applicator (1) in one hand, preferably between the thumb and the index finger. Once the user has selected the hair strands to be treated, said hair strand, preferably said bundle of hair strands, is located between said plate (10) and said containment portion (20) while the applicator (1) is in an open state. Subsequently said internal surface (101) of said plate (10) is brought into a juxtaposed relationship to said opening (203) of said well (20). Said applicator (1) is swiped along the length of said hair strand, preferably on said bundle of hair strands, and one or more hair treatment compositions are applied. More preferably, said hair treatment applicator (1) is located at the root-line of said hair strand, preferably at the root-line of said bundle of hair strands. The hair treatment composition may also be applied only to limited areas of the hair, i.e. the user can coat only the root-line with the hair treatment composition. The swiping may be repeated more than once, preferably twice.

Finally, the application of the hair treatment composition may occur on wet or dry hair and optionally, a rinsing or a shampooing step can be included between application of the first and second compositions to the hair.

6. Hair Treatment Compositions, Use Thereof and Kit

The present invention further comprises a kit. Said kit comprises an applicator (1) according to the invention and one or more individually packaged hair treatment compositions. Preferably, these compositions are selected from the group consisting of styling compositions, dyeing compositions, highlighting compositions or combination thereof. Each of these hair treatment compositions or combinations thereof may be used to provide a hair strand effect with said applicator (1) described above. More preferably, said one or more hair treatment composition is a highlighting composition.

Examples of hair treatment compositions which can be used with the hair treatment applicator (1) according to the invention are indicated below in table 1.

The hair treatment compositions may comprise components known, conventionally used, or otherwise effective for use in hair treatment compositions particularly oxidative bleaching and dye compositions which include but are not limited to: developer dye compounds; coupler dye compounds; direct dyes; oxidizing agents; reducing agents; thickeners; chelants; pH modifiers and buffering agents; alkalising agents, carbonate ion sources and radical scavenger systems; glycine; amodimethicone, ethylenediamine disuccinic acid; anionic, cationic, non-ionic, amphoteric or zwitterionic surfactants, or mixtures thereof; anionic, cationic, non-ionic, amphoteric or zwitterionic polymers, hydrophobically modified polymers or mixtures thereof; fragrances; dispersing agents; solvents, peroxide stabilizing agents; chelants, humectants, proteins and derivatives thereof, plant materials (e.g. aloe, chamomile and henna extracts); silicones (volatile or non-volatile, modified or non-modified), film-forming agents, cellulose polymers and their derivatives, ceramides, preserving agents, gel networks, colour indicators and opacifiers. Some adjuvants which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose. A representative but not exhaustive list of polymers and thickening agents can be found in "The Encyclopaedia of Polymers and Thickeners for Cosmetics" compiled and edited by Robert Y. Lochhead, PhD and William R. Fron, Department of Polymer Science, University of Southern Mississippi.

The present invention further comprises a kit. Said kit comprises an applicator (1) as described above and one or more individually packaged hair treatment compositions. More than one applicator (1) may be comprised in said kit.

In one embodiment of the present invention, said one or more individually packaged hair treatment compositions comprise a first individually packaged hair treatment composition and a second individually packaged hair treatment composition. When mixed said first and second individually packaged hair treatment compositions form a third hair treatment composition. Examples of such compositions include so called semi-permanent and permanent colorants which typically contain oxidative dyes and an oxidant, and highlighting compositions containing an oxidant and an alkalising agent, optionally with a persulfate salt. Preferably, said first individually packaged composition comprises an oxidizing agent and said second individually packaged composition comprises an alkalizing agent. Preferably, said oxidizing agent is hydrogen peroxide. More preferably, at least one of said first and/or second individually packaged hair treatment composition comprises a persulfate salt.

In one embodiment of the kit according to the present invention said first individually packaged hair treatment composition comprises from 3% to 12% of hydrogen peroxide by weight of said first individually packaged hair treatment composition and said second individually packaged hair treatment composition is in the form of a powder or paste activator and said second individually packaged hair treatment composition comprises from 10% to 60% of persulfate salt selected from sodium persulfate, potassium persulfate, ammonium persulfate or mixtures thereof, by weight of said second individually packaged hair treatment composition. Said kit optionally comprises a third individually packaged hair treatment composition comprising from 3% to 25% of an alkalizing agent in an aqueous vehicle, by weight of said third individually packaged hair treatment composition.

In another embodiment of the present invention said first individually packaged hair treatment composition comprises from 1.5% to 12% of hydrogen peroxide by weight of said first individually packaged hair treatment composition and said second individually packaged hair treatment composition comprises from 0.01% to 6% of a dye selected from direct dyes, oxidative dye precursors, oxidative dye couplers or mixtures thereof, by weight of said second individually packaged hair treatment composition.

Additional individually packaged hair treatment compositions may be present in the kit and may comprise shampoos, conditioner or styling products.

Herein below are given some examples of hair treatment compositions which are loaded into the hair treatment applicator (1) according to the invention. Each of the applicator embodiments described herein utilised with the compositions described herein below resulted in an application to the hair which was easy and simple and delivered an even application of the composition to the hair without any snagging or consumer discomfort.

A hair bleaching composition was prepared by mixing about 45 g of any of the formulations of Phase 1 (1.1, 2.1, 3.1, 4.1, table 1), which were in a liquid form with about 15 g of any of the formulations of Phase 2 (1.2, 2.2, 3.2, 4.2, in table 1), which were in a powder form. Mixing was achieved as follows: the powder formulation of Phase 2 was placed into a mixing tray and the liquid formulation of Phase 1 was poured on top of the powder. The two formulations were then mixed together using a spatula to form a bleaching composition. Mixing was completed when the bleaching composition looked visually homogeneous.

TABLE 1

Formulations of Phase 1 and 2 which can be mixed to form a highlighting composition.

| Phase 1 | 1.1 | 2.1 | 3.1 | 4.1 |
|---|---|---|---|---|
| De-ionized Water | q.s. to 100% | q.s. to 100% | q.s. to 100% | q.s. to 100% |
| Hydrogen Peroxide (35% Active) | 17.2 | 17.2 | 17.2 | 17.2 |
| Disodium EDTA | 0.04 | 0.04 | 0.04 | 0.04 |
| Sodium Hydroxide (50% aq. Solution) | q.s. to pH 3.5 | q.s. to pH 3.5 | q.s. to pH 3.5 | q.s. to pH 3.5 |
| Stearyl Alcohol [1] | 2 | 1 | 2 | 2 |
| Cetyl Alcohol [2] | 3 | 1.5 | 3 | 3 |
| Ceteareth 25 [3] | 1.5 | 0.75 | 1.5 | 1.5 |
| Aculyn ™ 33 [4] | | 2.4 | | |
| Salcare ™ SC 90 [5] | | | 1 | |

TABLE 1-continued

Formulations of Phase 1 and 2 which can be mixed to form a highlighting composition.

| Phase 2 | 1.2 | 2.2 | 3.2 | 4.2 |
|---|---|---|---|---|
| Ammonium Persulfate | 28.6 | 28.6 | 28.6 | 28.6 |
| Potassium Persulfate | 50 | 50 | 50 | 47 |
| Sodium Persulfate | 7.14 | 7.14 | 7.14 | 7.14 |
| Sodium Metasilicate | 14.26 | 14.26 | 14.26 | 14.26 |
| Carbopol ™ Ultrez 10 [6] | | | | 3 |

All ingredients are in percentage by weight of the formulation phase.
[1] Stearyl Alcohol Crodacol S-95, Croda, Inc.
[2] Cetyl Alcohol, Crodacol C-70, Croda, Inc.
[3] Cetearth 25, Cremophor A 25, BASF Corporation
[4] Aculyn ™ 33, Rohm and Hass Company Inc.
[5] Salcare ™ SC 90 Ciba Specialty Chemicals Corporation
[6] Carbopol ™ Ultrez 10

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator (1) for applying a hair treatment composition to the hair, wherein said applicator (1) comprises a plate (10) and a well (20), wherein said plate (10) and well (20) are movably joined by a connection (30) so that the applicator (1) may alternate between a closed and an open state, and wherein said plate (10) has an external surface (102) and an internal surface (101), and said internal surface (101) comprises at least one hair orientation means which extends beyond said internal surface (101) towards said well (20), and wherein said well (20) comprises a rim (222) and wherein said applicator (1) further comprises a liquid impervious, resilient fluid metering means, wherein said fluid metering means comprises a lower metering means (50) positioned on said rim (222) of said well (20), and an upper metering means (60) positioned on said internal surface (101) of said plate (10), wherein said lower and upper metering means (50, 60) are each independently tubular, wherein said lower and upper metering means (50, 60), each independently comprise an inner and an outer surface, wherein said outer surface of said upper metering means (60) and said outer surface of said lower metering means (50) independently have a convex shape and wherein when said applicator (1) is in said closed state, said lower metering means (50) and said upper metering means (60) are substantially juxtaposed to provide said fluid metering means.

2. The applicator (1) according to claim 1, wherein said lower metering means (50) is substantially a mirror image of said upper metering means (60).

3. The applicator (1) according to claim 1, wherein said fluid metering means is selected from thermoplastic elastomers.

4. The applicator (1) according to claim 1, wherein said lower metering means (50) and said upper metering means (60) are positioned adjacent said connection (30).

5. The applicator (1) according to claim 1, wherein said lower metering means (50) is continuous and said upper metering means (60) is continuous.

6. The applicator according to claim 1, wherein said upper and lower metering means (60, 50) are each independently hollow.

7. The Applicator according to claim 1, wherein said upper and lower metering means (50, 60) have a substantially semi-elliptical cross section.

8. The Applicator according to claim 1, wherein said upper metering means (60) is positioned substantially parallel to the perimeter (103) of said internal surface (101) of said plate (10) and said lower metering layer (50) is positioned substantially parallel to said rim (222) of said well (20).

9. A method to apply a hair treatment composition with said applicator (1) according to claim 1, to a hair strand, wherein said method comprises applying a hair treatment composition to said applicator (1) in said open state, selecting a bundle of hair strands, placing said hair strands in said applicator (1) and bringing said applicator (1) into said closed position and then swiping said applicator (1) along the length of said hair strand.

10. A kit-of parts comprising an applicator (1) according to claim 1; and one or more individually packaged hair treatment compositions, and instructions for use.

11. Use of an applicator according to claim 1, with one or more hair treatment compositions or combinations thereof to provide a hair strand effect wherein the applicator (1) is loaded with said one or more hair treatment compositions prior to providing the hair strand effect.

12. An applicator (1) for applying a hair treatment composition to the hair, wherein said applicator (1) comprises a plate (10) and a well (20), wherein said plate (10) and well (20) are movably joined by a connection (30) so that the applicator (1) may alternate between a closed and an open state, and wherein said plate (10) has an external surface (102) and an internal surface (101), and said internal surface (101) comprises at least one hair orientation means which extends beyond said internal surface (101) towards said well (20), and wherein said well (20) comprises a rim (222) and wherein said applicator (1) further comprises a liquid impervious, resilient fluid metering means, wherein said fluid metering means comprises a lower metering means (50) positioned on said rim (222) of said well (20), and an upper metering means (60) positioned on said internal surface (101) of said plate (10), wherein said upper and lower metering means (60, 50) independently comprise two portions (50; 50') (60; 60'), wherein said lower and upper metering means (50, 60), each independently comprise an inner and an outer surface, wherein said outer surface of said upper metering means (60) and said outer surface of said lower metering means (50) independently have a convex shape and wherein when said applicator (1) is in said closed state, said lower metering means (50) and said upper metering means (60) are substantially juxtaposed to provide said fluid metering means.

13. The applicator (1) according to claim 12, wherein said lower metering means (50) is substantially a mirror image of said upper metering means (60).

14. The applicator (1) according to claim 12, wherein said fluid metering means is selected from thermoplastic elastomers.

15. The applicator (1) according to claim 12, wherein said lower metering means (50) and said upper metering means (60) are positioned adjacent said connection (30).

16. The applicator (1) according to claim 12, wherein said lower metering means (50) is continuous and said upper metering means (60) is continuous.

17. The applicator according to claim 12, wherein said upper and lower metering means (60, 50) are each independently hollow.

18. A kit-of parts comprising an applicator (1) according to claim 12; and one or more individually packaged hair treatment compositions, and instructions for use.

* * * * *